(12) United States Patent
Grichnik

(10) Patent No.: US 11,191,500 B2
(45) Date of Patent: Dec. 7, 2021

(54) PORTABLE BARIUM SWALLOW TEST APPARATUS

(71) Applicant: James Grichnik, Hawthorn Woods, IL (US)

(72) Inventor: James Grichnik, Hawthorn Woods, IL (US)

(*) Notice: Subject to any disclaimer, the term of this patent is extended or adjusted under 35 U.S.C. 154(b) by 0 days.

(21) Appl. No.: 17/129,879

(22) Filed: Dec. 21, 2020

(65) Prior Publication Data

US 2021/0275118 A1 Sep. 9, 2021

Related U.S. Application Data

(60) Provisional application No. 62/951,766, filed on Dec. 20, 2019.

(51) Int. Cl.
*A61B 6/00* (2006.01)

(52) U.S. Cl.
CPC .............. *A61B 6/4405* (2013.01); *A61B 6/40* (2013.01); *A61B 6/4233* (2013.01); *A61B 6/4441* (2013.01); *A61B 6/467* (2013.01); *A61B 6/481* (2013.01); *A61B 6/50* (2013.01); *A61B 6/54* (2013.01)

(58) Field of Classification Search
CPC ..... A61B 6/4405; A61B 6/548; A61B 6/4423; A61B 6/102; A61B 6/4441; A61B 6/547; A61B 6/4225; A61B 6/447; A61B 6/4007; A61B 6/032; A61B 6/4411; A61B 44/52; G06T 2207/10116
See application file for complete search history.

(56) References Cited

U.S. PATENT DOCUMENTS 5,586,162 A 12/1996 Grichnik
2018/0242935 A1* 8/2018 Bouvier .................. A61B 6/102

* cited by examiner

*Primary Examiner* — Don K Wong

(57) ABSTRACT

A portable barium test apparatus is used to perform Modified Barium Swallow Studies (MBSS) on patients in different locations, such as the home of the patient or a care facility. The apparatus includes a hand truck, a U-shaped support, a height-adjusting track, a support carriage, an X-ray generator, and an image-capturing device. The hand truck allows the medical staff to transport the apparatus to the desired location to perform the procedure. The U-shaped support maintains the X-ray generator and the image-capturing device at the desired arrangement to perform the procedure. The height-adjusting track enables the repositioning of the U-shaped support at the desired height to accommodate the patient. The support carriage connects the U-shaped support to the height-adjusting track and maintains the arrangement of the U-shaped support during the procedure. The X-ray generator and the image-capturing device enable the medical staff to perform the MBSS procedure on the patient.

19 Claims, 13 Drawing Sheets

PORTABLE BARIUM SWALLOW TEST APPARATUS

The current application claims a priority to the U.S. Provisional Patent application Ser. No. 62/951,766 filed on Dec. 20, 2019. The current application is filed on Dec. 21, 2020 while Dec. 20, 2020 was on a weekend.

FIELD OF THE INVENTION

The present invention generally relates to medical equipment and portable devices. More specifically, the present invention is a portable test apparatus designed to test patients suffering from conditions where swallowing may be difficult.

BACKGROUND OF THE INVENTION

The Modified Barium Swallow Studies (MBSS) are tests designed to diagnose patients experiencing swallowing issues. Medical conditions where patients have trouble swallowing are one of the leading causes of death in the United States. Dysphagia is a condition defined as difficulty in swallowing, and the transfer of solids or liquids from the mouth to the stomach. Dysphagia affects eating, drinking, taking oral medication, and even swallowing saliva. Elderly patients have a higher risk of suffering from such conditions, and the numbers are expected to rise as the populations ages. When patients experience symptoms of Dysphagia, the MBSS allow physicians to visualize in real time the factors that may cause these symptoms and possible compensatory strategies. However, the high costs of these tests often deter people from taking them in the first place, increasing the chances for serious health issues and even death. As an example, in the early 1990's, the cost of providing MBSS to nursing home patients became cost prohibitive with one of the main reasons being the increasing cost of medical transport. To conduct the appropriate testing, the patient must be transported to a medical facility where trained staff and equipment is available. Thus, to overcome these issues, the MBSS apparatuses were adapted to better suit the needs of the patients. As such, various testing apparatuses have been made to be transported to facilities where patients have limited mobility. Unfortunately, conducting MBSS on patients receiving household care can be a dauting task due to the physical size and scale of these apparatuses. The present invention aims to solve these issues by providing a mobile apparatus designed to be operational in numerous locations including elderly care facilitates or private homes.

The present invention takes various design features into consideration to ensure the apparatus performs as expected including, but not limited to, ease of transportation, adaptability to various home entrance designs, ability to overcome internal home obstacles, and integration of MBSS imaging & data processing. In addition, the present invention keeps a total weight under two hundred and fifty pounds, integrated transport system, adaptable U-arm design, adjustable pivot, and integrated X-ray imaging capabilities. Furthermore, the present invention includes a modular design that allows for convenient transport and storage methods as well as for transport in all weather conditions.

SUMMARY OF THE INVENTION

The present invention is an apparatus designed to allow medical personnel to conduct Modified Barium Swallow Studies (MBSS) in the comfort of the patients' home. With the increasing market of elderly care conducted at home, the need arose for an MBSS apparatus designed to be operational in the patient's home. In addition, the present invention is designed to accommodate patients that are wheelchair bound, without the need to remove the patient from the wheelchair. Furthermore, the present invention is adaptable to patients of various shapes and sizes, while still providing consistent and accurate results. The present invention operates on household voltages and has a rugged construction; therefore, the present invention is operational in a variety of temperatures and conditions.

DETAILED DESCRIPTION OF THE INVENTION

All illustrations of the drawings are for the purpose of describing selected versions of the present invention and are not intended to limit the scope of the present invention.

Figure 1:
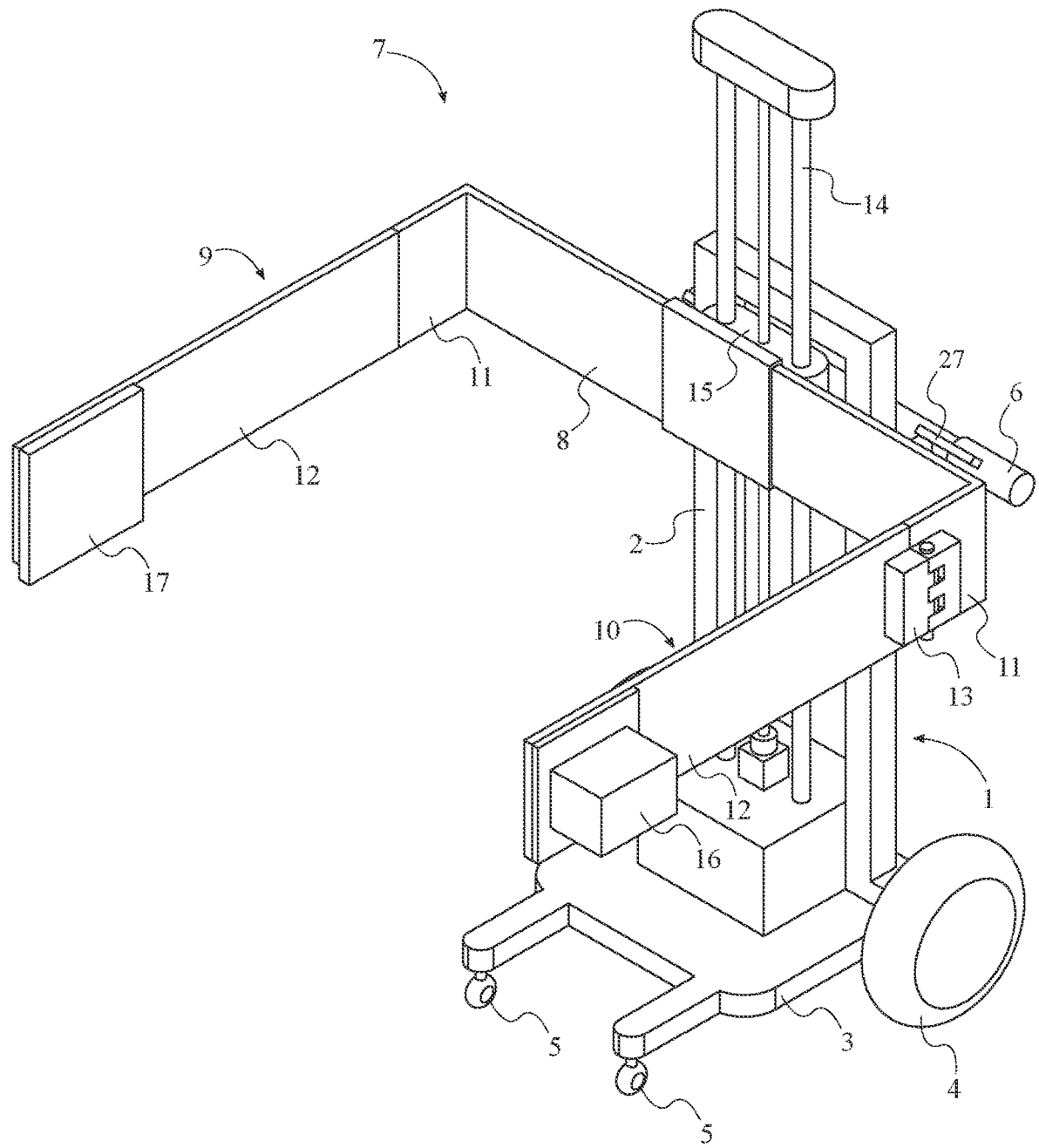
FIG. 1 is a top-front-left perspective view showing the present invention.
Figure 2:
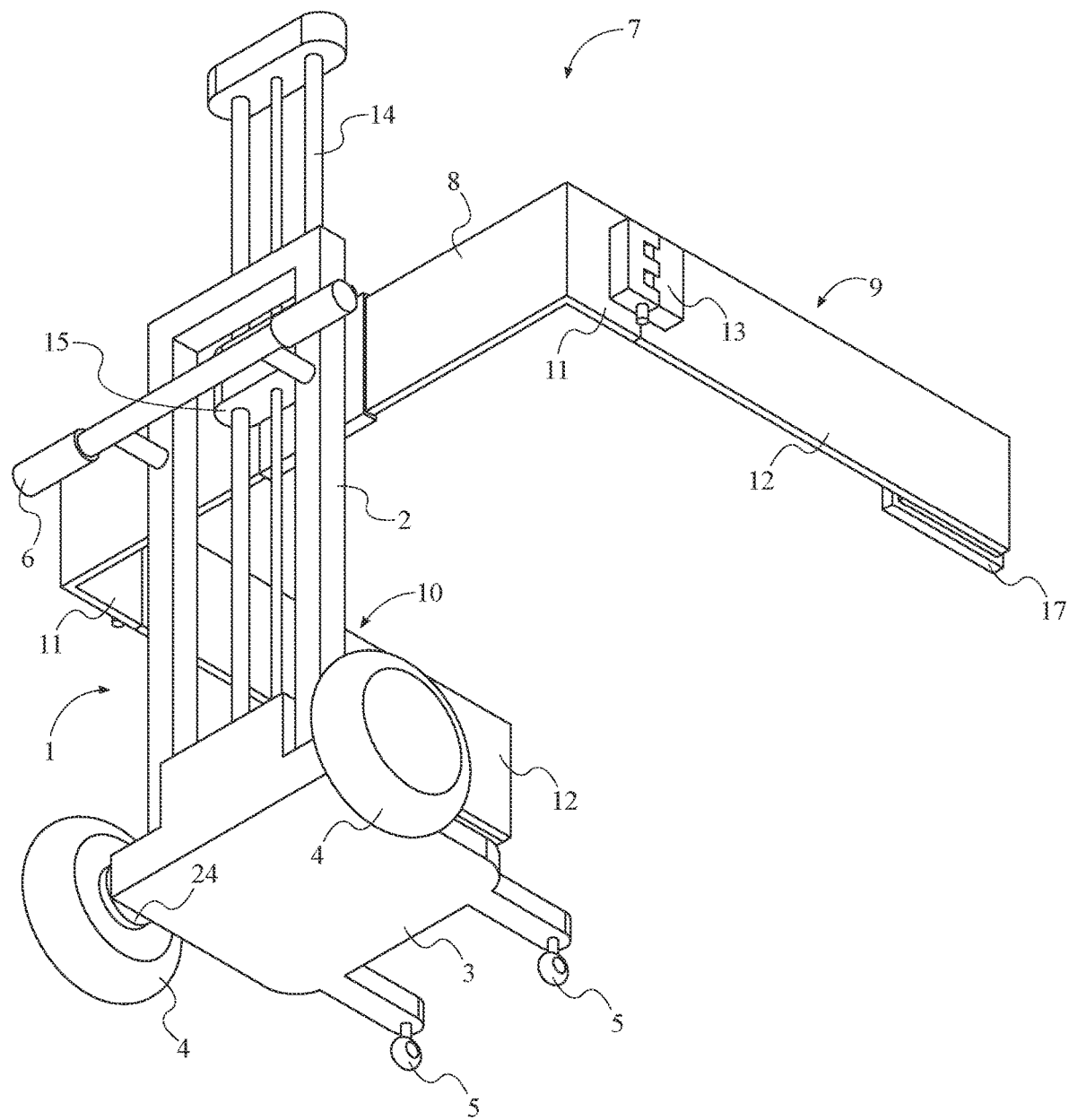
FIG. 2 is a bottom-rear-right perspective view showing the present invention.

The present invention is a portable barium test apparatus which enables medical staff to perform Modified Barium Swallow Studies (MBSS) on patients in different locations, such as the home of the patient or a care facility. As can be seen in FIGS. 1 and 2, the present invention may comprise a hand truck 1, a U-shaped support 7, a height-adjusting track 14, a support carriage 15, an X-ray generator 16, and an image-capturing device 17. The hand truck 1 allows the medical staff to transport the present invention to the desired location to perform the MBSS on a patient. The U-shaped support 7 maintains the X-ray generator 16 and the image-capturing device 17 at the desired arrangement to perform the MBSS on the patient. The height-adjusting track 14 enables the repositioning of the U-shaped support 7 at the desired height to accommodate the patient. The support carriage 15 connects the U-shaped support 7 to the height-adjusting track 14 and maintains the arrangement of the U-shaped support 7 during the procedure. The X-ray generator 16 and the image-capturing device 17 enable the medical staff to perform the MBSS on the patient.

The general configuration of the aforementioned components allows MBSS to be performed at the patient's location instead of having the patient come to a medical facility. As can be seen in FIGS. 1 and 2, the hand truck 1 comprises an elongated frame 2, a wheeled base 3, and a handlebar assembly 6 to enable the user to manually transport the present invention across different terrains and obstacles. The U-shaped support 7 comprises a support web 8, a first support arm 9, and a second support arm 10 to keep the X-ray generator 16 and the image-capturing device 17 at the necessary arrangement to perform the MBSS. The wheeled base 3 is terminally mounted to the elongated frame 2 so that the wheeled base 3 supports the elongated frame 2 and the U-shaped support 7. In addition, the elongated frame 2 is preferably positioned perpendicular to the wheeled base 3 to form an upright structure. The handlebar assembly 6 is laterally mounted to the elongated frame 2, offset from the wheeled base 3, to enable the user to manually control the movement of the hand truck 1. The handlebar assembly 6 may comprise multiple grip portions for the user to handle, and the grip portions may be covered with grip material to increase the coefficient of friction between the hands of the user and the grip portions. The height-adjusting track 14 is laterally mounted along the elongated frame 2, opposite to the handlebar assembly 6, to enable the movement of the U-shaped support 7 along the elongated frame 2. Thus, the user can adjust the height of the U-shaped support 7 from the ground to accommodate different heights of patients.

Figure 6:
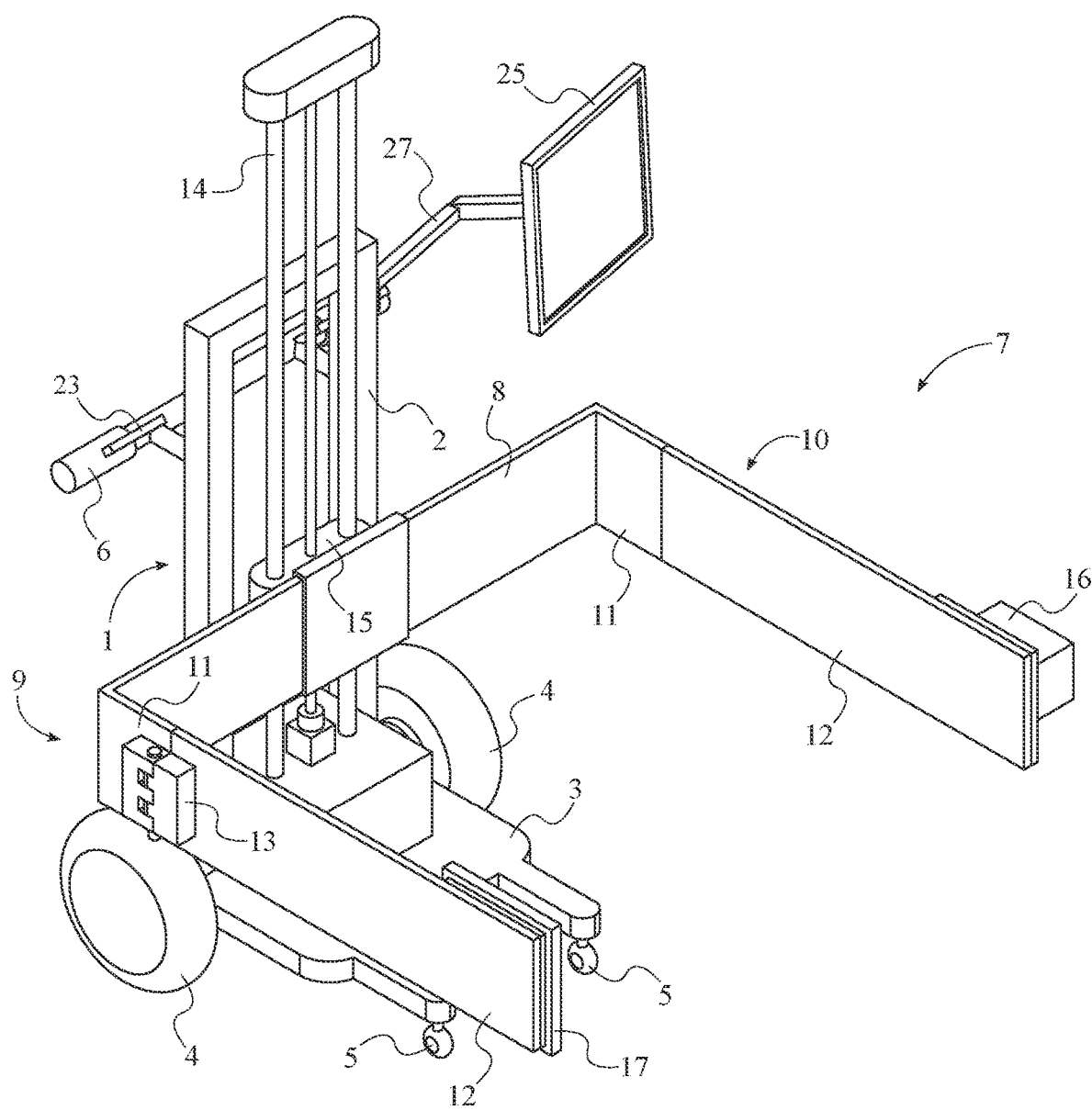
FIG. 6 is a top-front-right perspective view showing the present invention with the user interface, wherein the U-shaped support is shown lowered.

As can be seen in FIGS. 1 and 6, the first support arm 9 is terminally connected to the support web 8. Likewise, the second support arm 10 is terminally connected to the support web 8, opposite to the first support arm 9, to form the U shape of the U-shaped support 7 along with the first support arm 9. The support web 8 is movably mounted to the height-adjusting track 14 by the support carriage 15 so that the user can choose the position of the support web 8 along the height-adjusting track 14 to adjust the height of the U-shaped support 7. Furthermore, the X-ray generator 16 is laterally mounted to the first support arm 9, offset from the support web 8, to emit X-rays to be utilized to visualize in real-time the desired internal body areas. On the other hand, the image-capturing device 17 is laterally mounted to the second support arm 10, offset from the support web 8, to capture the emitted X-rays to generate the live imaging of the patient. In some embodiments, the height-adjusting track 14 can be a manually operated mechanism that the user can engage to manually move the support carriage 15 along the height-adjusting track 14. For example, a gear assembly operatively may be integrated into the height-adjusting track 14 to move the support carriage 15 along the height-adjusting track 14. A hand crank may be operatively connected to the gear assembly so that the user can manually engage the gear assembly. In other embodiments, an automated mechanism may be integrated into the height-adjusting track 14 to automatically move the support carriage 15 along the height-adjusting track 14 to a desired location. For example, a set of linear actuators or a hydraulics system may be operatively integrated into the height-adjusting track 14 to move the support carriage 15 along the height-adjusting track 14 to a predetermined location.

Figure 3:
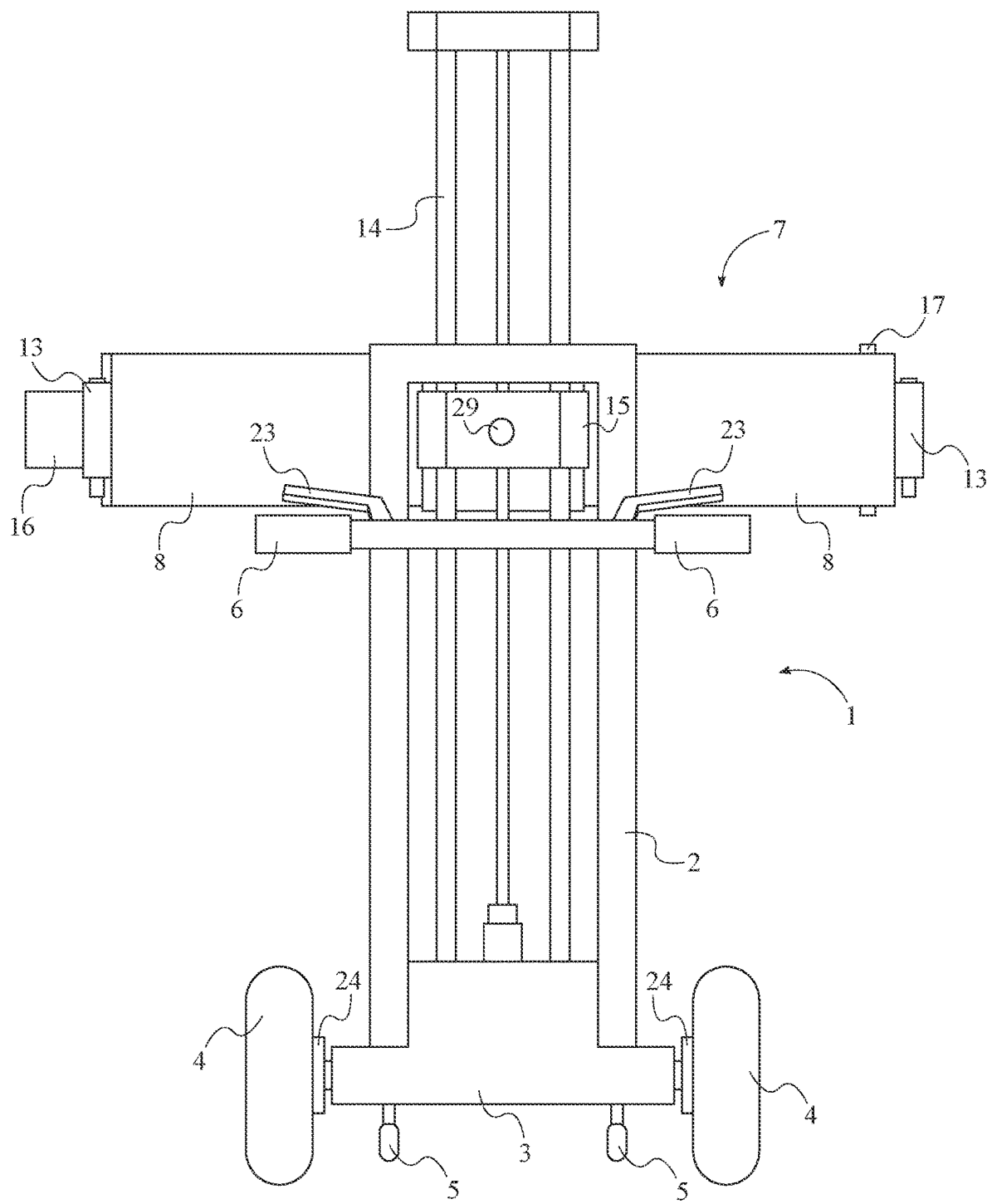
FIG. 3 is a rear view showing the present invention.

As can be seen in FIGS. 2 and 3, to enable the medical staff to maneuver the hand truck 1 around different areas and obstacles, the present invention may further comprise at least one spring-loaded lever 23 and a brake mechanism 24. In addition, the wheeled base 3 may comprise a pair of drive wheels 4 to enable the movement of the hand truck 1. The at least one spring-loaded lever 23 is hingedly connected to the handlebar assembly 6 so that the user can remotely engage the brake mechanism 24. The at least one spring-loaded lever 23 is operatively coupled to the brake mechanism 24, wherein the at least one spring-loaded lever 23 is used to actuate the brake mechanism 24. For example, the at least one spring-loaded lever 23 can be connected to the brake mechanism 24 by a transmission mechanism such as a Bowden cables or hydraulic hoses. The transmission mechanism can be mounted within the elongated frame 2 and the wheeled base 3 or positioned external to the hand truck 1. Further, the brake mechanism 24 is operatively integrated into the pair of drive wheels 4, wherein the brake mechanism 24 is used to decelerate the rotation of the pair of drive wheels 4. For example, the brake mechanism 24 can be a pair of caliper brakes or drum brakes connected to the corresponding rims of the pair of drive wheels 4. In one embodiment, the at least one spring-loaded lever 23 may be two spring-loaded levers, and each of the spring-loaded levers is operatively coupled to a corresponding drive wheel of the pair of drive wheels 4. The user can selectively engage the corresponding brake mechanism 24 on one of the pair of drive wheels 4 or both. Thus, the user can pivot the hand truck 1 in narrow and tight spots by locking one drive wheel at a time. In other embodiments, the brake mechanism 24 can be modified to accommodate different types of drive wheels.

Figure 5:
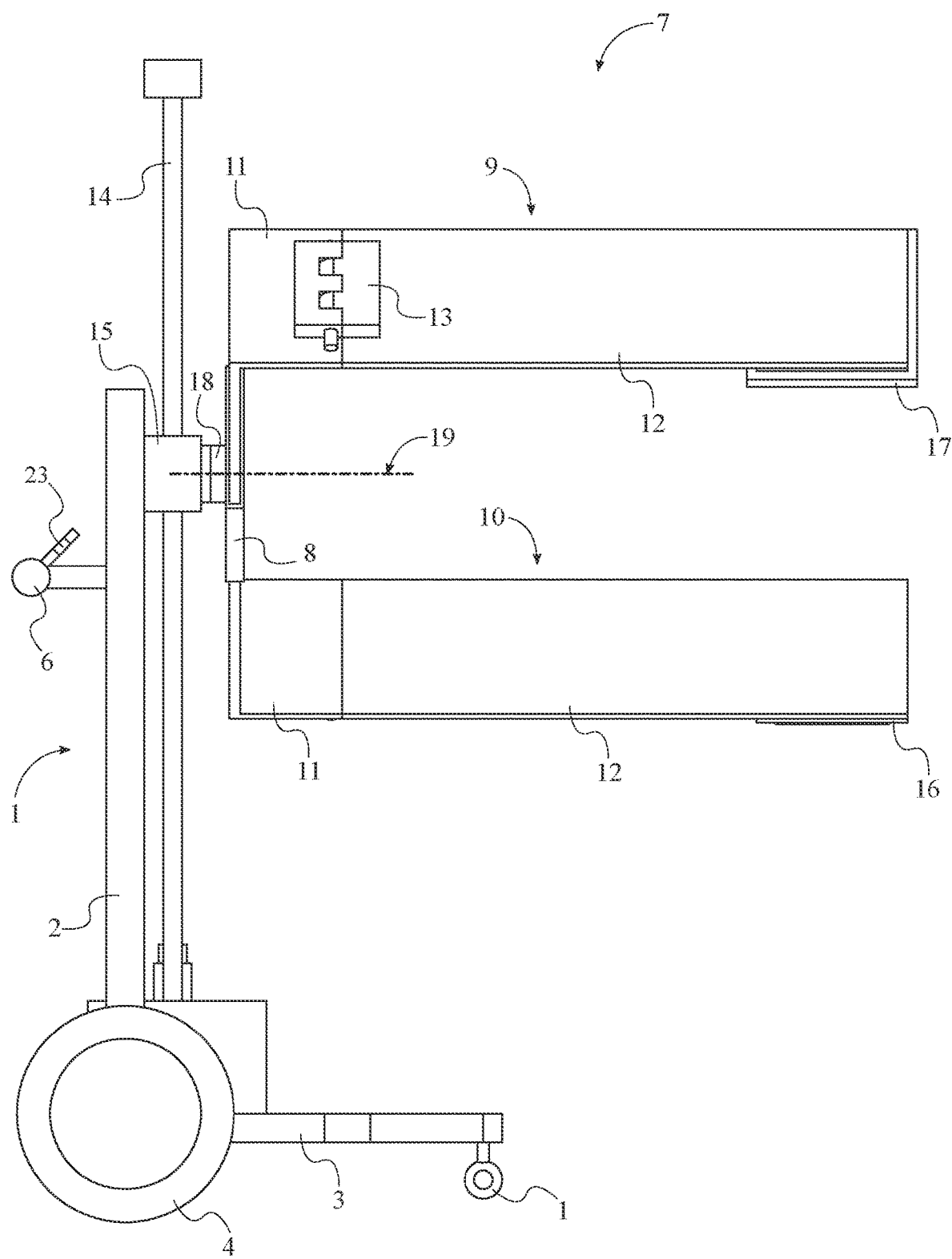
FIG. 5 is a side view showing the U-shaped support of the present invention in a tilted configuration.

In addition to the pair of drive wheels 4, the wheeled base 3 may further comprise a plurality of casters 5 to provide balance to the hand truck 1 when standing upright. As can be seen in FIGS. 2 and 5, the plurality of casters 5 is positioned offset from the pair of drive wheels 4 to create a wide stabilization base. Also, the plurality of casters 5 is positioned adjacent to the U-shaped support 7. Thus, the plurality of casters 5 prevents the hand truck 1 from tipping forward when the hand truck 1 is standing upright. Further, the plurality of casters 5 can enable the standing movement of the hand truck 1 if quick repositioning is necessary. In other embodiments, the wheeled base 3 can utilize different mechanisms to stand upright and balanced during the MBSS procedure.

Figure 4:
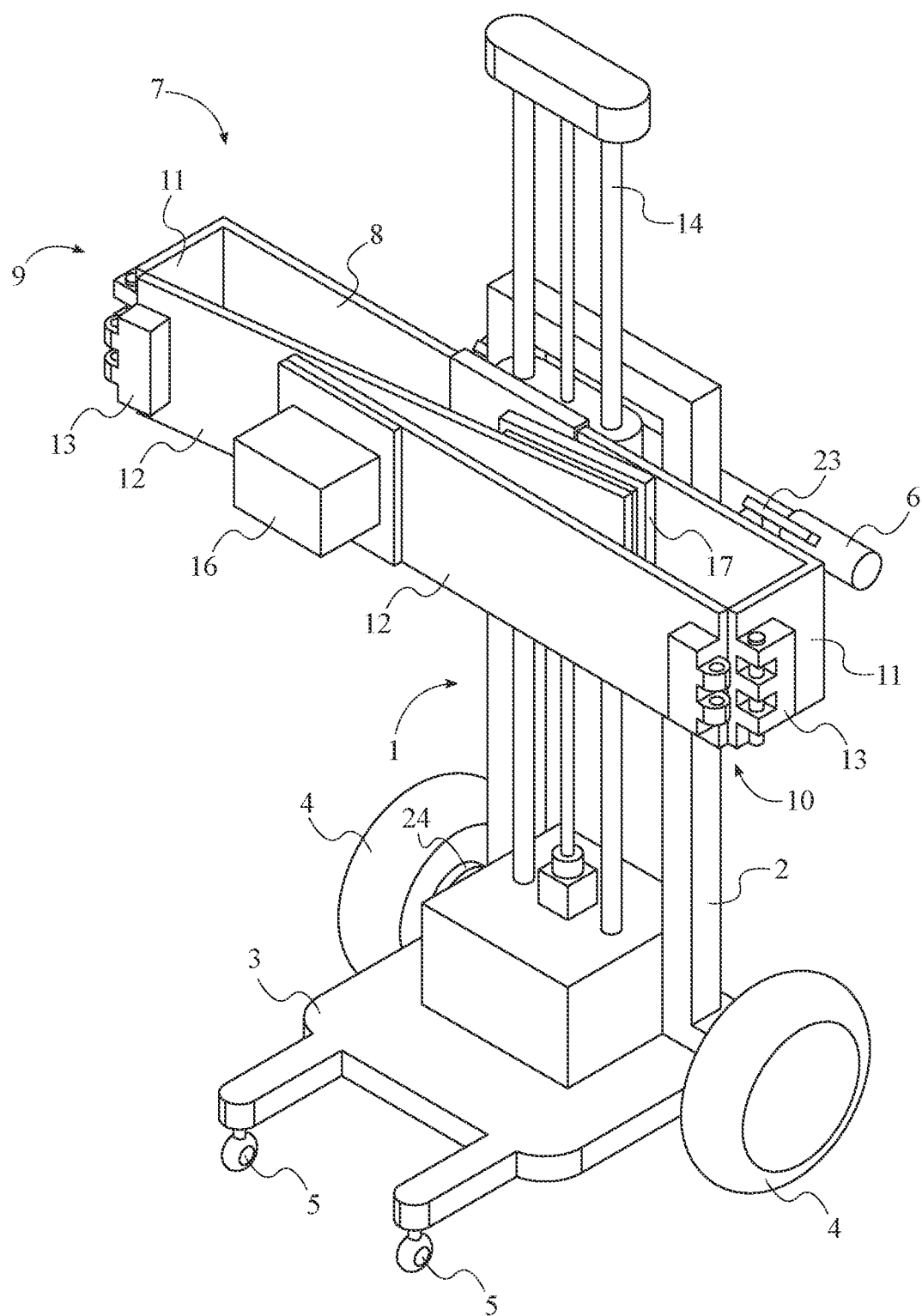
FIG. 4 is a top-front-left perspective view showing the U-shaped support of the present invention in a folded configuration.

To increase the portability of the present invention, the U-shaped support 7 can be designed as a foldable structure to be easily folded up and stowed away in vehicle. As can be seen in FIGS. 1 and 4, the first support arm 9 and the second support arm 10 each comprises a proximal arm portion 11, a distal arm portion 12, and a lockable hinge mechanism 13 to enable the folding of each arm for storage and easier mobility of the hand truck 1 in tight spaces. The support web 8 is terminally connected to the proximal arm portion 11 to maintain the first support arm 9 and the second support arm 10 connected to the support web 8 by its corresponding proximal arm portion 11. The distal arm portion 12 is terminally positioned to the proximal arm portion 11, opposite to the support web 8, and positioned collinear to the proximal arm portion 11 to form an elongated arm structure. Further, the distal arm portion 12 is rotatably connected to the proximal arm portion 11 by the lockable hinge mechanism 13 to enable the user to fold the U-shaped support 7 for storage or to deploy the U-shaped support 7 to conduct the MBSS procedure. The lockable hinge mechanism 13 enables the user to lock the distal arm portion 12 in the desired position. Alternatively, the lockable hinge mechanism 13 for each arm can be positioned at the connection between the respective arm and the support web 8. In addition, the lockable hinge mechanism 13 maintains calibration even when the first support arm 9 or the second support arm 10 is folded. For example, in a deployed configuration, the distal arm portion 12 is positioned parallel to the proximal arm portion 11 and locked in place to extend the corresponding arm to enable the user to conduct the MBSS procedure. On the other hand, in a stored configuration, the distal arm portion 12 is positioned perpendicular to the proximal arm portion 11, against the support web 8, and locked in place so that the present invention can fit inside tight spaces.

As previously mentioned, the present invention provides various features to accommodate the patient for the MBSS procedure in different locations and positions. As can be seen in FIG. 5, the present invention may further comprise a yaw-adjusting mechanism 18 which enables the user to adjust the yaw angle of the U-shaped support 7. The yaw-adjusting mechanism 18 enables the rotation of the U-shaped support 7 on the yaw axis up to an angle, such as twenty degrees, to prevent the hand-truck from tilting sideways from any momentum. The support web 8 is rotatably connected to the support carriage 15 by the yaw-adjusting mechanism 18 to enable the rotation of the support web 8 about the yaw-adjusting mechanism 18. A rotation axis 19 of the yaw-adjusting mechanism 18 is positioned perpendicular to the support web 8. Likewise, the rotation axis 19 of the yaw-adjusting mechanism 18 is positioned perpendicular to the heigh-adjusting track. Thus, the U-shaped support 7 can be rotated about the support carriage 15 to adjust the yaw angle of the U-shaped support 7 to accommodate patients with different needs. For example, the fully adjustable U-shaped support 7 allows medical staff to test patients who are wheelchair bound, without the need to move the patient from the wheelchair or the bed.

Figure 9:
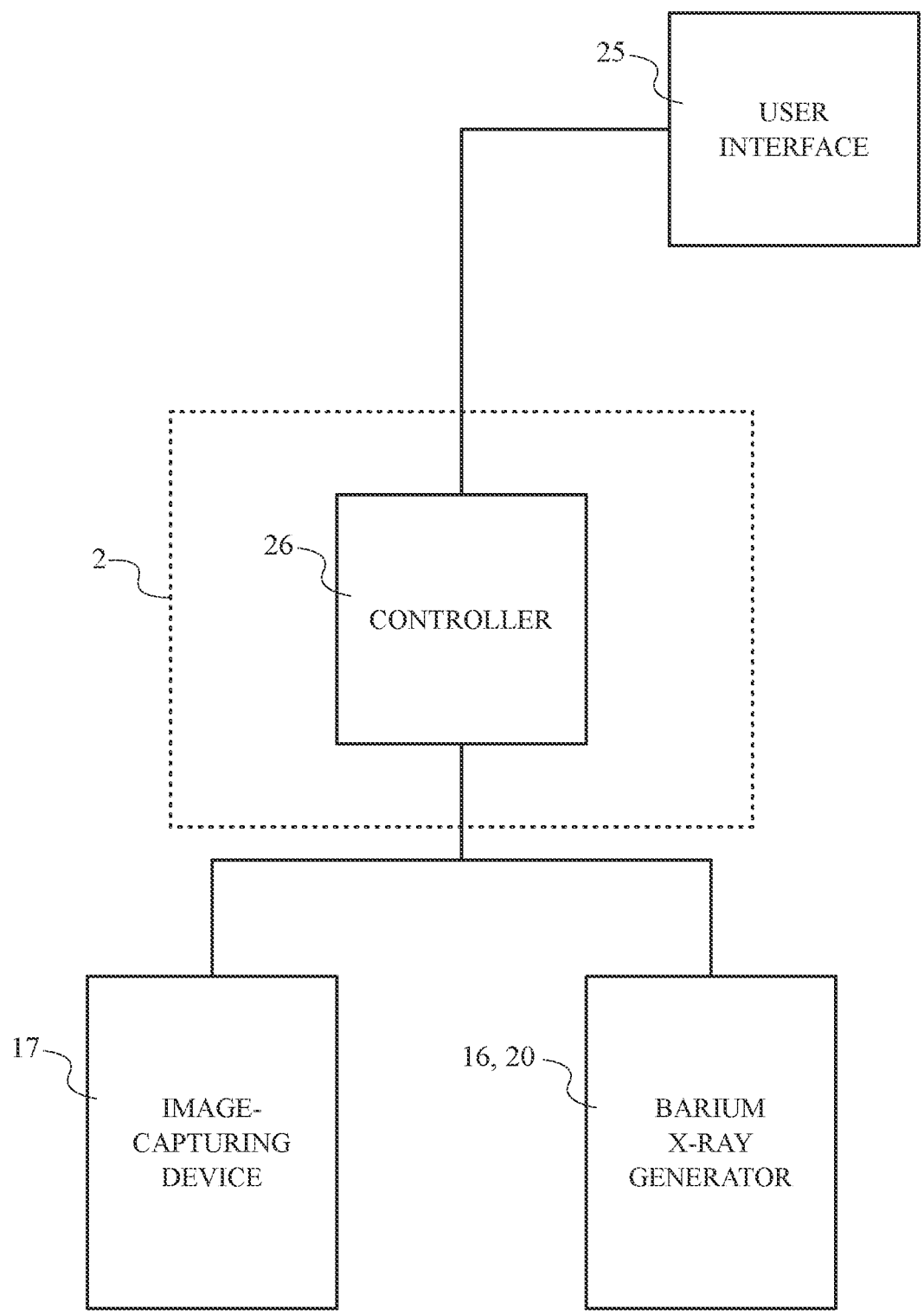
FIG. 9 is a schematic view showing the X-ray generator of the present invention as a barium X-ray generator.
Figure 10:
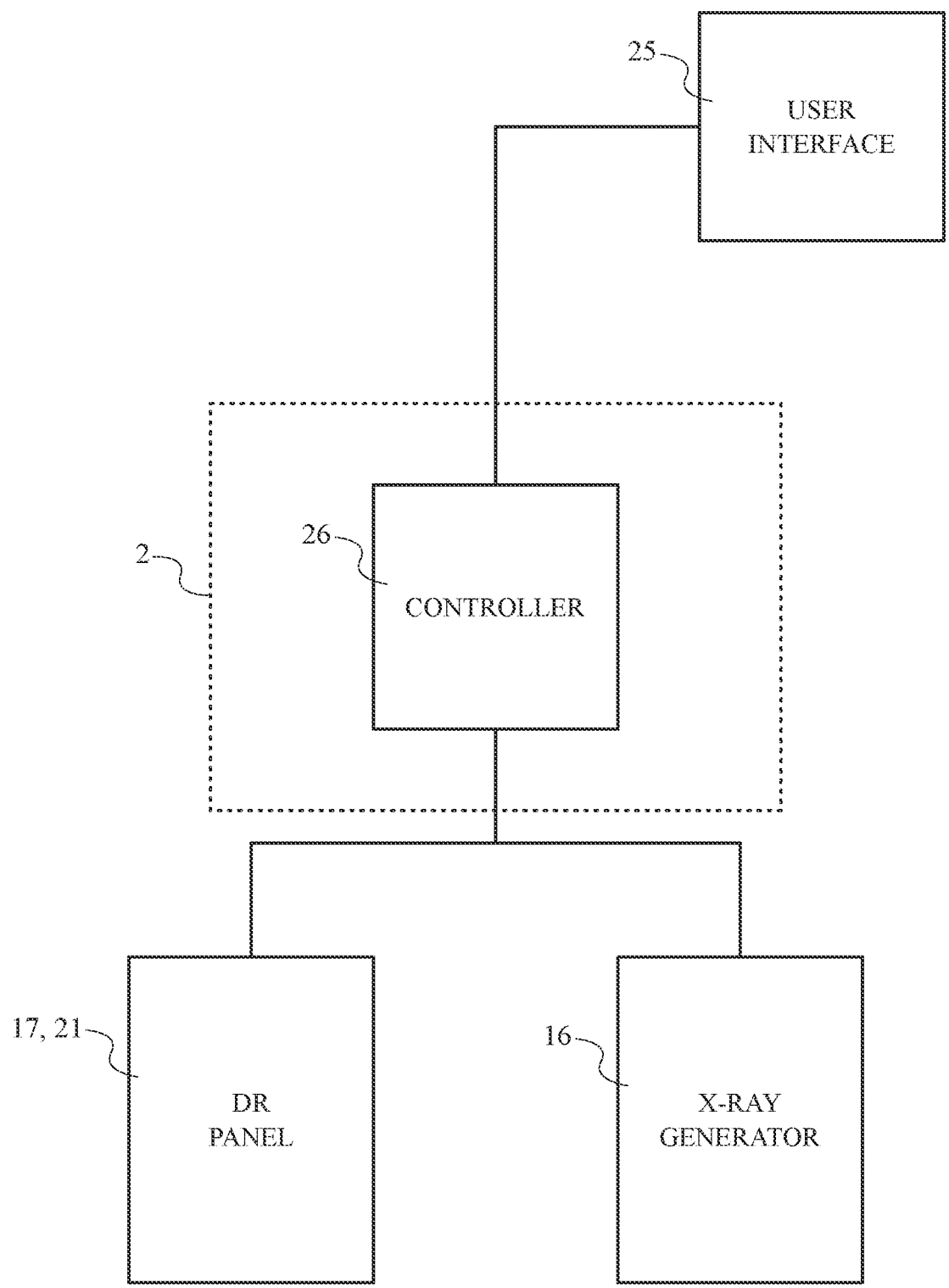
FIG. 10 is a schematic view showing the image-capturing device of the present invention as a digital radiography (DR) panel.
Figure 11:
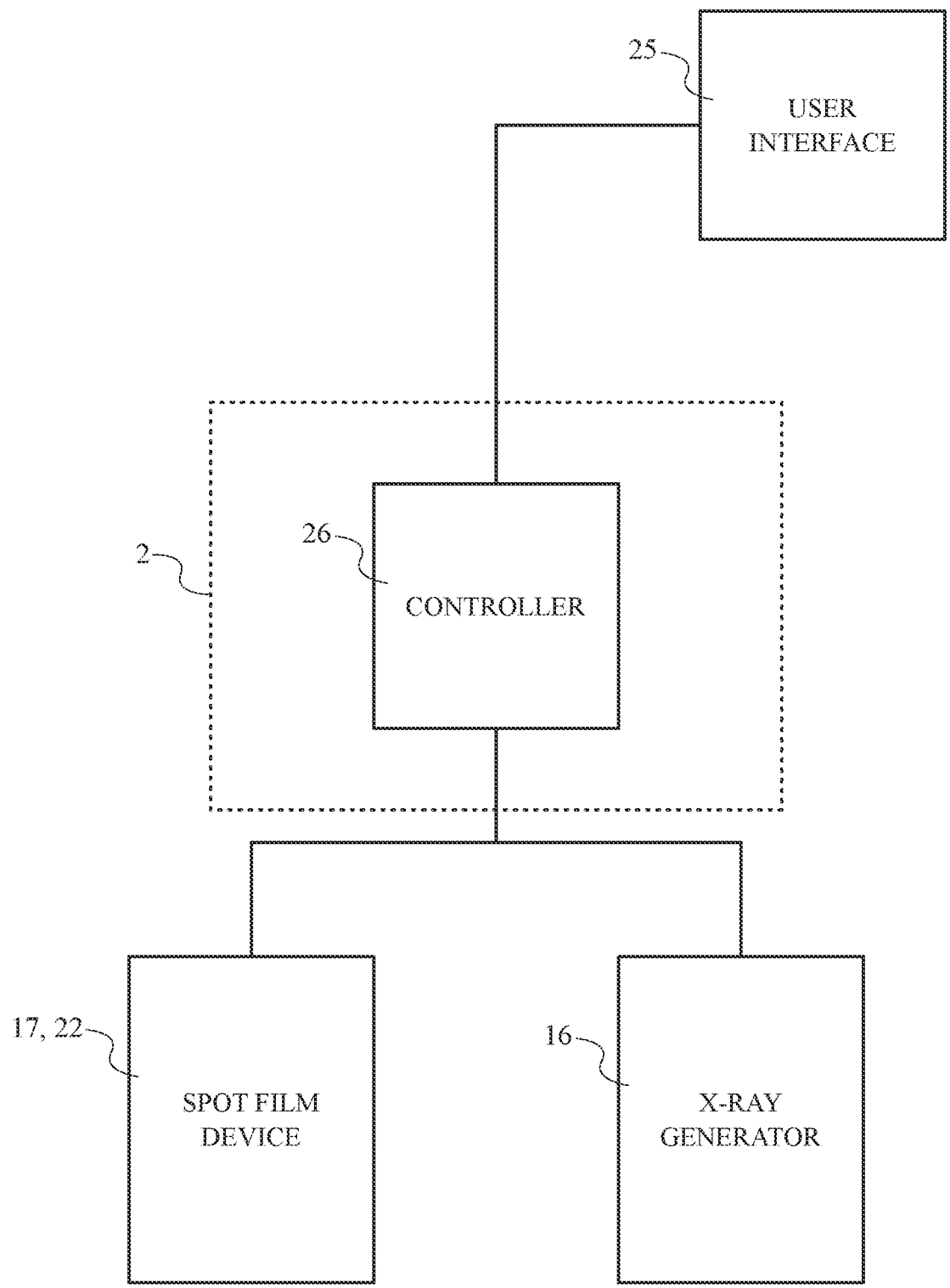
FIG. 11 is a schematic view showing the image-capturing device of the present invention as a spot film device.

To enable the medical staff to perform the necessary MBSS procedure, the present invention can utilize different imaging technologies which can be interchanged as necessary. As can be seen in FIGS. 9 through 11, the X-ray generator 16 is preferably a barium X-ray generator 20 to perform barium X-ray examinations of the gastrointestinal (GI) tract. Further, the image-capturing device 17 is preferably a digital radiography (DR) panel 21 designed to digitally capture the X-ray generated data to be transmitted. Furthermore, the image-capturing device 17 is preferably a spot film device 22 designed to receive a radiographic film cassette to obtain radiographs during the procedure. The X-ray generator 16 and the image-capturing device 17 can be set up for either the barium X-ray examination or a fluoroscopy examination. In other embodiments, the present invention can utilize different imaging technologies or be connected to external medical devices.

Figure 8:
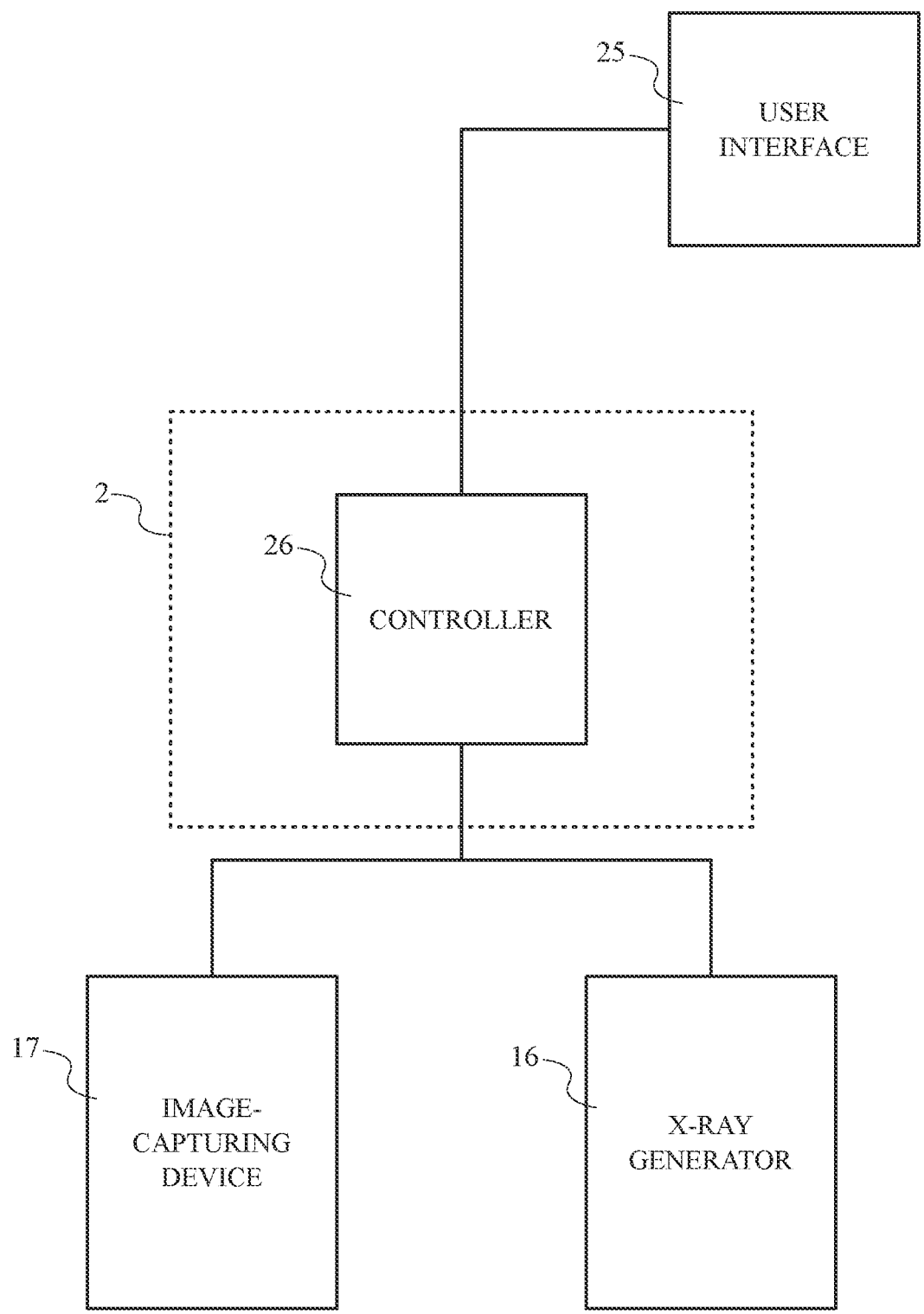
FIG. 8 is a schematic view showing the electronic connections to the controller of the present invention.

To facilitate the MBSS procedure, the present invention may further comprise a user interface 25 and a controller 26 that enables the medical staff to monitor and control the procedure. As can be seen in FIGS. 6 and 8, the user interface 25 is laterally mounted to the elongated frame 2, offset from the wheeled base 3, so the user interface 25 does not obstruct with the operation of the hand truck 1. The user interface 25 is also positioned adjacent to the handlebar assembly 6 to provide easy access to the user. Further, the controller 26 is mounted within the elongated frame 2 to protect all electronics from damage. The controller 26 is electronically connected to the user interface 25, the X-ray generator 16, and the image-capturing device 17 so that the controller 26 oversees the operation of the user interface 25, the X-ray generator 16, and the image-capturing device 17. Thus, the user can configure the operation of the X-ray generator 16 and the image-capturing device 17 from the user interface 25 while the controller 26 controls the operation of the image-capturing device 17 and the X-ray generator 16 during the procedure. Further, data from the image-capturing device 17 is transmitted to the controller 26 and the user interface 25 so the user can observe in real time the results of the procedure. In other embodiments, the controller 26 may include a transmitter to wirelessly transmit the procedure data to a remote server.

Figure 7:
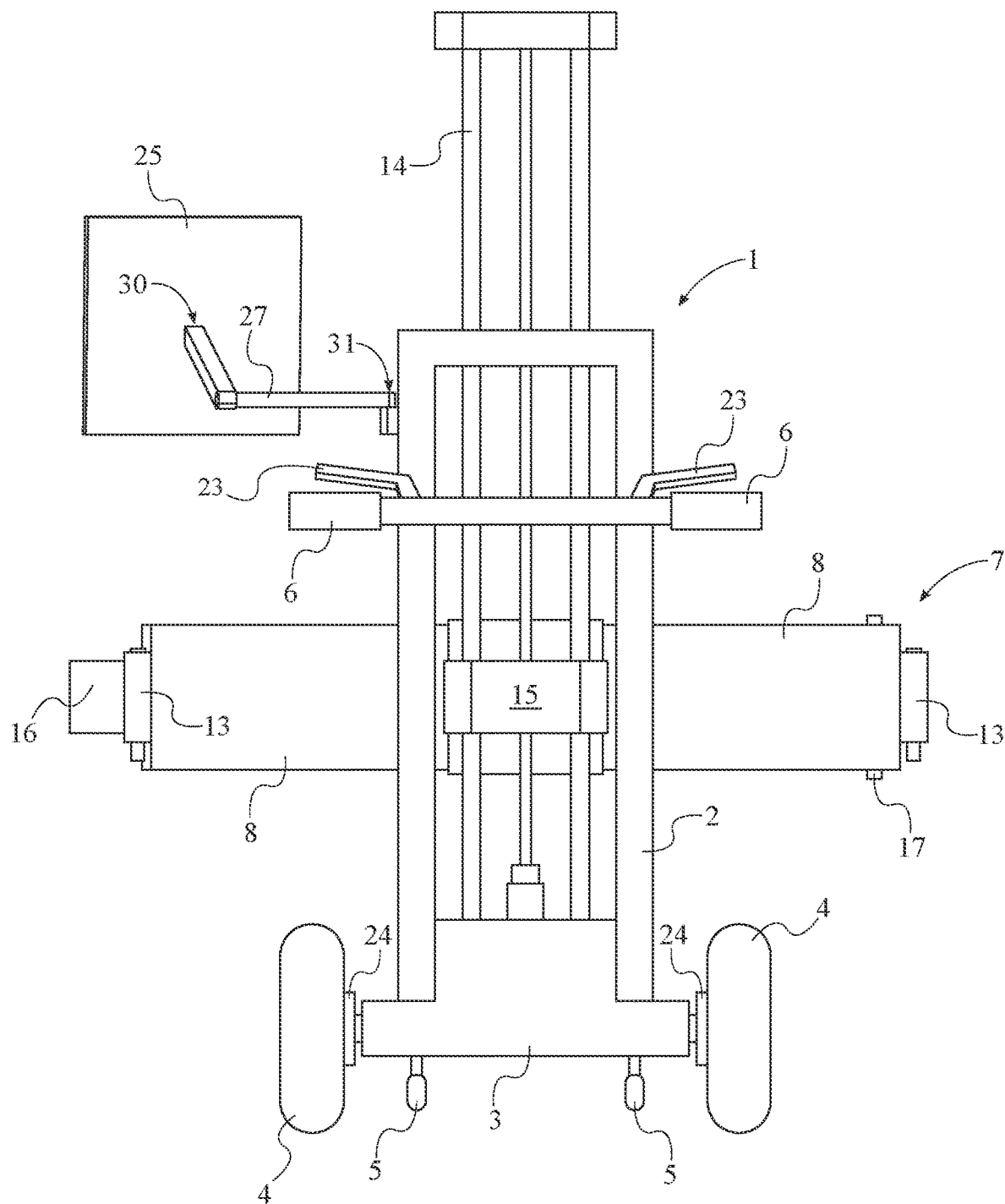
FIG. 7 is a rear view showing the present invention with the user interface, wherein the U-shaped support is shown lowered.

As can be seen in FIGS. 6 and 7, the present invention may further comprise a foldable arm 27 to reposition the user interface 25 and to keep the medical staff at a safe distance during MBSS procedure. The foldable arm 27 comprises a proximal arm end 30 and a distal arm end 31. The proximal arm end 30 is laterally mounted to the elongated frame 2 to secure the foldable arm 27 to the elongated frame 2. Further, the proximal arm end 30 is positioned in between the height-adjusting track 14 and the handlebar assembly 6 to prevent the foldable arm 27 from obstructing the movement of the U-shaped support 7. The user interface 25 is mounted onto the distal arm end 31 so that the user interface 25 is supported by the foldable arm 27.

Figure 12:
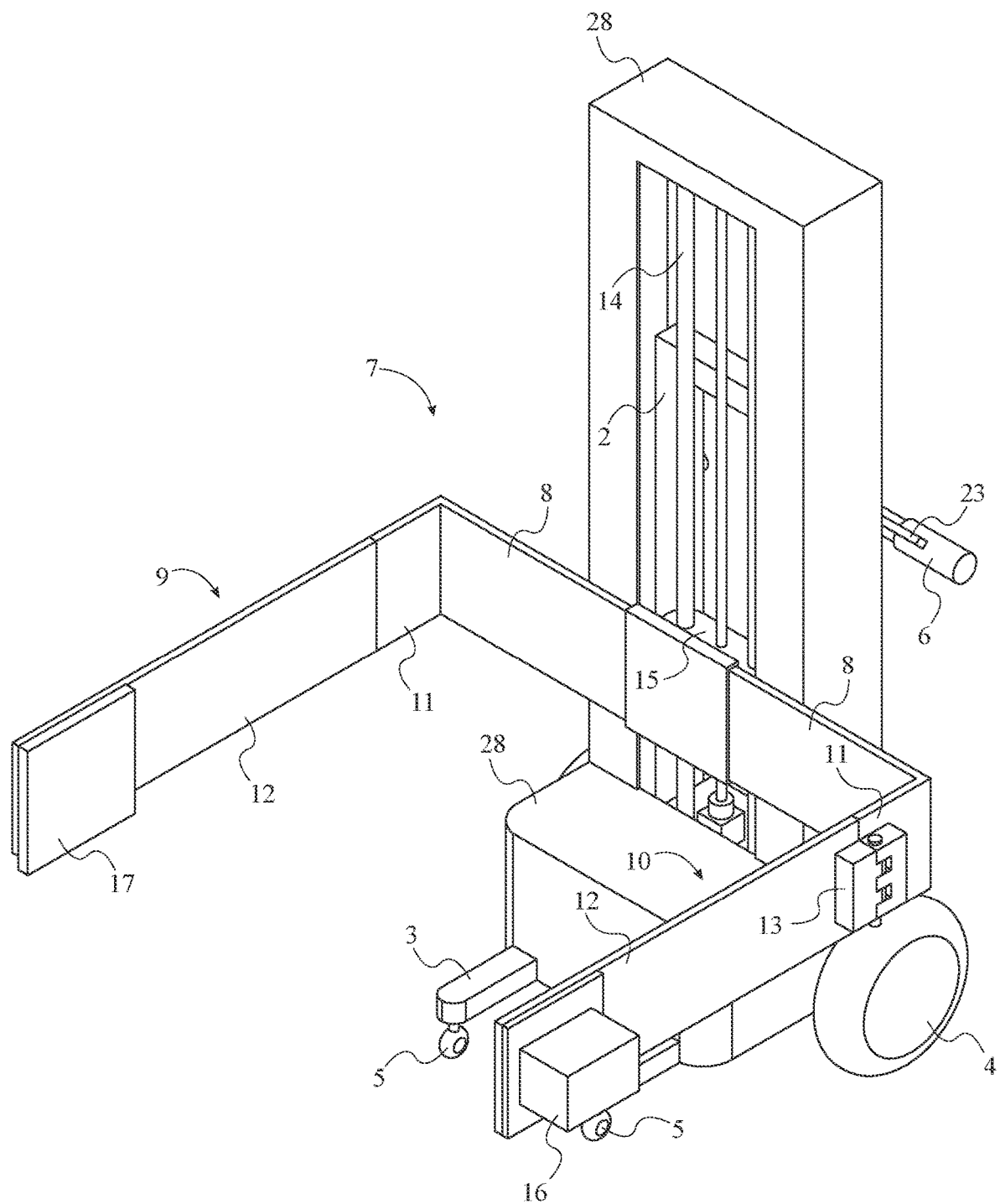
FIG. 12 is a top-front-left perspective view showing the present invention with a housing.
Figure 13:
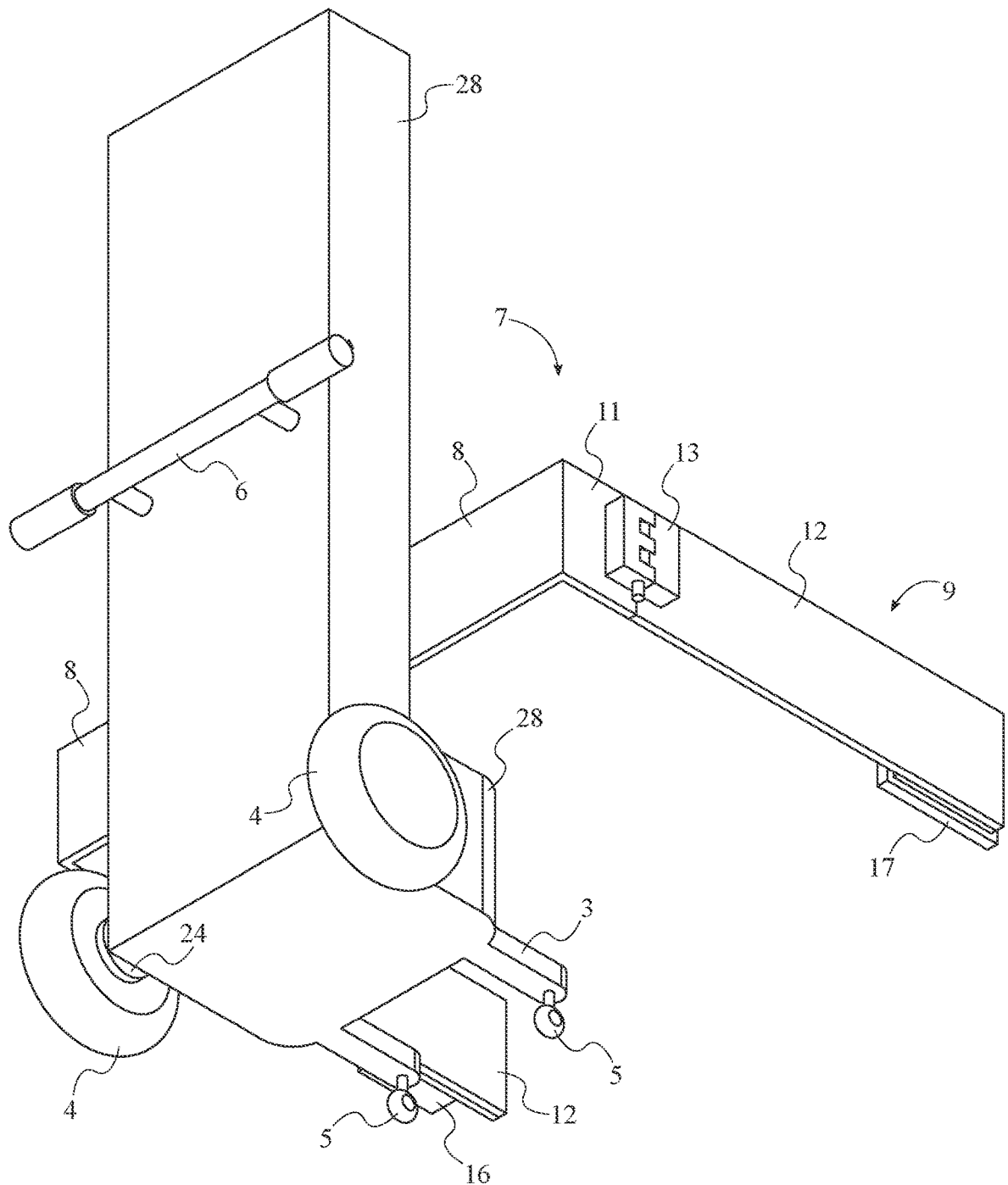
FIG. 13 is a bottom-rear-right perspective view showing the present invention with the housing.

Further, to cover the internal structure of the present invention and provide a rugged construction, the present invention may further comprise a housing 28. As can be seen in FIGS. 12 and 13, the housing 28 is mounted about the height-adjusting track 14, the support carriage 15, the elongated frame 2, and the support web 8 to provide an aesthetically pleasing look. The housing 28 may include a plurality of housing panels designed to match the shape and design of the corresponding internal components in the height-adjusting track 14, the support carriage 15, the elongated frame 2, and the support web 8. Further, each of the plurality of housing panels may be easily removable for easy maintenance.

Finally, to maintain the U-shaped support 7 at the desired height, the present invention may further comprise a translational locking mechanism 29. As can be seen in FIG. 3, the translational locking mechanism 29 is operatively coupled in between the support carriage 15 and the height-adjusting track 14, wherein the translational locking mechanism 29 is used to selectively lock the support carriage 15 at a specific height along the height-adjusting track 14. For example, the translational locking mechanism 29 may be a spring-loaded pin lock that automatically engages with one hole of multiple holes distributed along the height-adjusting track 14. The user can release the spring-loaded pin lock, relocate the U-shaped support 7, and let the spring-loaded pin lock engage with the corresponding new hole. In alternate embodiments, a different translational locking mechanism 29 may be utilized.

Although the invention has been explained in relation to its preferred embodiment, it is to be understood that many other possible modifications and variations can be made without departing from the spirit and scope of the invention as hereinafter claimed.

What is claimed is:

1. A portable barium swallow test apparatus comprising:
a hand truck;
a U-shaped support;
a height-adjusting track;
a support carriage;
an X-ray generator;
an image-capturing device;
the hand truck comprising an elongated frame, a wheeled base, and a handlebar assembly;

the U-shaped support comprising a support web, a first support arm, and a second support arm;

the wheeled base being terminally mounted to the elongated frame;

the handlebar assembly being laterally mounted to the elongated frame, offset from the wheeled base;

the height-adjusting track being laterally mounted along the elongated frame, opposite to the handlebar assembly;

the first support arm being terminally connected to the support web;

the second support arm being terminally connected to the support web, opposite to the first support arm;

the support web being movably mounted to the height-adjusting track by the support carriage;

the X-ray generator being laterally mounted to the first support arm, offset from the support web; and, the image-capturing device being laterally mounted to the second support arm, offset from the support web.

2. The portable barium swallow test apparatus as claimed in claim 1 comprising:

at least one spring-loaded lever;

a brake mechanism;

the wheeled base comprising a pair of drive wheels;

the at least one spring-loaded lever being hingedly connected to the handlebar assembly;

the at least one spring-loaded lever being operatively coupled to the brake mechanism, wherein the at least one spring-loaded lever is used to actuate the brake mechanism; and, the brake mechanism being operatively integrated into the pair of drive wheels, wherein the brake mechanism is used to decelerate rotation of the pair of drive wheels.

3. The portable barium swallow test apparatus as claimed in claim 2 comprising:

the wheeled base further comprising a plurality of casters;

the plurality of casters being positioned offset from the pair of drive wheels; and, the plurality of casters being positioned adjacent to the U-shaped support.

4. The portable barium swallow test apparatus as claimed in claim 1 comprising:

the first support arm and the second support arm each comprising a proximal arm portion, a distal arm portion, and a lockable hinge mechanism;

the support web being terminally connected to the proximal arm portion;

the distal arm portion being terminally positioned to the proximal arm portion, opposite to the support web; and, the distal arm portion being rotatably connected to the proximal arm portion by the lockable hinge mechanism.

5. The portable barium swallow test apparatus as claimed in claim 1 comprising:

a yaw-adjusting mechanism;

the support web being rotatably connected to the support carriage by the yaw-adjustment mechanism;

a rotation axis of the yaw-adjusting mechanism being positioned perpendicular to the support web; and, the rotation axis of the yaw-adjusting mechanism being positioned perpendicular to the height-adjusting track.

6. The portable barium swallow test apparatus as claimed in claim 1, wherein the X-ray generator is a barium X-ray generator.

7. The portable barium swallow test apparatus as claimed in claim 1, wherein the image-capturing device is a digital radiography (DR) panel.

8. The portable barium swallow test apparatus as claimed in claim 1, wherein the image-capturing device is a spot film device.

9. The portable barium swallow test apparatus as claimed in claim 1 comprising:

a user interface;

a controller;

the user interface being laterally mounted to the elongated frame, offset from the wheeled base;

the user interface being positioned adjacent to the handlebar assembly;

the controller being mounted within the elongated frame; and, the controller being electronically connected to the user interface, the X-ray generator, and the image-capturing device.

10. The portable barium swallow test apparatus as claimed in claim 9 comprising:

a foldable arm;

the foldable arm comprising a proximal arm end and a distal arm end;

the proximal arm end being laterally mounted to the elongated frame;

the proximal arm end being positioned in between the height-adjusting track and the handlebar assembly; and, the user interface being mounted onto the distal arm end.

11. The portable barium swallow test apparatus as claimed in claim 1 comprising:

a housing; and, the housing being mounted about the height-adjusting track, the support carriage, the elongated frame, and the support web.

12. The portable barium swallow test apparatus as claimed in claim 1 comprising:

a translational locking mechanism; and, the translational locking mechanism being operatively coupled in between the support carriage and the height-adjusting track, wherein the translational locking mechanism is used to selectively lock the support carriage at a specific height along the height-adjusting track.

13. A portable barium swallow test apparatus comprising:

a hand truck;

a U-shaped support;

a height-adjusting track;

a support carriage;

an X-ray generator;

an image-capturing device;

the hand truck comprising an elongated frame, a wheeled base, and a handlebar assembly;

the U-shaped support comprising a support web, a first support arm, and a second support arm;

the first support arm and the second support arm each comprising a proximal arm portion, a distal arm portion, and a lockable hinge mechanism;

the wheeled base being terminally mounted to the elongated frame;

the handlebar assembly being laterally mounted to the elongated frame, offset from the wheeled base;

the height-adjusting track being laterally mounted along the elongated frame, opposite to the handlebar assembly;

the first support arm being terminally connected to the support web;

the second support arm being terminally connected to the support web, opposite to the first support arm;

the support web being movably mounted to the height-adjusting track by the support carriage;

the X-ray generator being laterally mounted to the first support arm, offset from the support web;

the image-capturing device being laterally mounted to the second support arm, offset from the support web;

the support web being terminally connected to the proximal arm portion;

the distal arm portion being terminally positioned to the proximal arm portion, opposite to the support web; and, the distal arm portion being rotatably connected to the proximal arm portion by the lockable hinge mechanism.

14. The portable barium swallow test apparatus as claimed in claim 13 comprising:

at least one spring-loaded lever;

a brake mechanism;

the wheeled base comprising a pair of drive wheels;

the wheeled base further comprising a plurality of casters;

the at least one spring-loaded lever being hingedly connected to the handlebar assembly;

the at least one spring-loaded lever being operatively coupled to the brake mechanism, wherein the at least one spring-loaded lever is used to actuate the brake mechanism;

the brake mechanism being operatively integrated into the pair of drive wheels, wherein the brake mechanism is used to decelerate rotation of the pair of drive wheels;

the plurality of casters being positioned offset from the pair of drive wheels; and, the plurality of casters being positioned adjacent to the U-shaped support.

15. The portable barium swallow test apparatus as claimed in claim 13 comprising:

a yaw-adjusting mechanism;

a housing;

a translational locking mechanism;

the support web being rotatably connected to the support carriage by the yaw-adjustment mechanism;

a rotation axis of the yaw-adjusting mechanism being positioned perpendicular to the support web;

the rotation axis of the yaw-adjusting mechanism being positioned perpendicular to the height-adjusting track;

the housing being mounted about the height-adjusting track, the support carriage, the elongated frame, and the support web; and, the translational locking mechanism being operatively coupled in between the support carriage and the height-adjusting track, wherein the translational locking mechanism is used to selectively lock the support carriage at a specific height along the height-adjusting track.

16. The portable barium swallow test apparatus as claimed in claim 13, wherein the X-ray generator is a barium X-ray generator.

17. The portable barium swallow test apparatus as claimed in claim 13, wherein the image-capturing device is a digital radiography (DR) panel.

18. The portable barium swallow test apparatus as claimed in claim 13, wherein the image-capturing device is a spot film device.

19. The portable barium swallow test apparatus as claimed in claim 13 comprising:

a user interface;

a controller;

a foldable arm;

the foldable arm comprising a proximal arm end and a distal arm end;

the user interface being laterally mounted to the elongated frame, offset from the wheeled base;

the user interface being positioned adjacent to the handlebar assembly;

the controller being mounted within the elongated frame;

the controller being electronically connected to the user interface, the X-ray generator, and the image-capturing device;

the proximal arm end being laterally mounted to the elongated frame;

the proximal arm end being positioned in between the height-adjusting track and the handlebar assembly; and, the user interface being mounted onto the distal arm end.

* * * * *